United States Patent [19]

Argiriardi

[11] 4,042,368

[45] Aug. 16, 1977

[54] ADDITIVE FOR QUATERNARY AMINE BACTERICIDES AND ALGICIDES, COMPOSITIONS CONTAINING SAME AND METHOD OF MANUFACTURE

[75] Inventor: Andrew A. Argiriardi, Brooklyn, N.Y.

[73] Assignee: Epic Chemical Inc., Brooklyn, N.Y.

[21] Appl. No.: 590,977

[22] Filed: June 27, 1975

[51] Int. Cl.$^2$ .............................................. A01N 9/20
[52] U.S. Cl. ...................................... 71/67; 424/329; 260/567.6 M
[58] Field of Search ................ 260/567.6 M; 424/329; 71/67

[56] References Cited

U.S. PATENT DOCUMENTS

| | | | |
|---|---|---|---|
| 3,369,046 | 2/1968 | Kaniecki et al. | 260/567.6 M |
| 3,914,496 | 10/1975 | Jorek et al. | 260/567.6 M |
| 3,932,655 | 1/1976 | Conn | 424/329 |

Primary Examiner—V. D. Turner
Attorney, Agent, or Firm—Blum, Moscovitz, Friedman & Kaplan

[57] ABSTRACT

Tris(2-hydroxyethyl) benzyl ammonium chloride, although having a phenol coefficient lower than 1, when added to a quaternary amine, yields a composition in which the phenol coefficient of the quaternary amine is lowered by an amount which is much less than would correspond to the quantity of the tris(2-hydroxyethyl) benzyl ammonium chloride content thereof. As a result, a substantial savings in cost can be achieved. A method of manufacture is disclosed.

5 Claims, 2 Drawing Figures

ADDITIVE FOR QUATERNARY AMINE BACTERICIDES AND ALGICIDES, COMPOSITIONS CONTAINING SAME AND METHOD OF MANUFACTURE

BACKGROUND OF THE INVENTION

Quaternary amines, and, in particular, the benzalkonium chlorides have been found to be useful as bactericides and algicides. At lower concentrations they are baceteristats and aligistats. Perhaps the widest use for these compounds at the present time is in control of bacteria and algae in swimming pools as well as sanitizing dishes, cookware, sinks, bathrooms, toilets and floors and walls of dwellings, office buildings and restaurants. These compounds, while effective, are relatively expensive, even at the low concentrations in which they are used, so that means of lowering the cost of the use of such compounds while maintaining the same level of effectiveness is highly to be desired.

SUMMARY OF THE INVENTION

Applicant has found that the compound tris(2-hydroxyethyl) benzyl ammonium chloride, to be referred to herein hereafter as T-QUAT, can be added to the much more expensive and effective quaternary amines without a proportionate lowering of the effectiveness of such compounds, this, despite the fact that T-QUAT has a phenol coefficient which is less than 1. It should be noted that T-QUAT has substantial algicidal effect despite the lack of bactericidal effect. As a result of the fact that T-QUAT is so much less expensive than the usual quaternary amines, it becomes possible to achieve any desired level of effectiveness as measured by phenol coefficient by adding an appropriate quantity of T-QUAT to the effective quaternary amine and appropriately increasing the weight of composition used above that of the weight of quaternary amine when used alone.

Quaternary amines which have been found to be effective in combination with T-QUAT are the benzalkonium chlorides, the trimethyl alkyl chlorides and the alkyl-substituted imidazole chlorides. Ratios of T-QUAT to effective quaternary amine can range as high as about 9 to 1 while maintaining the bactericidal level at the desired value by increase in the quantity of composition used. Cost savings in excess of 36% can be achieved.

T-QUAT is easily synthesized by combining essentially equimolar quantities of triethanolamine and benzyl chloride. The reaction product can be used without purification. Furthermore, up to at least 90 mol % of the triethanolamine can be replaced with another amine such as alkyl dimethylamine, and the synthesis carried out in the same way. In other words, T-QUAT and the effective quaternary amine can be synthesized together. As before, the reaction product can be used without purification. Of course, if desired, the reaction products of both reactions can be purified.

Accordingly, an object of the present invention is a compound of lower cost than the bactericidal and algicidal quaternary amines which can be blended over a range of proportions with such quaternary amines to produce a composition having a bactericidal effect which is substantially greater than the weighted average of the components.

Another object of the present invention is a composition consisting essentially of T-QUAT and another quaternary amine having a high phenol coefficient where the phenol coefficient of the composition is substantially greater than the weighted average of the components.

A further object of the present invention is a method of synthesizing T-QUAT in both pure and impure form.

An important object of the present invention is a method of synthesizing T-QUAT and at least one other quaternary amine, said other quaternary amine having a high phenol coefficient, said T-QUAT and said other quaternary amine being synthesized together.

Still other objects and advantages of the invention will in part be obvious and will in part be apparent from the specification.

The invention accordingly comprises a method of synthesizing both a compound and a composition, the method comprising the several steps and the relation of one or more of such steps with respect to each of the others and the composition possessing the features, properties, and the relation of constituents which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
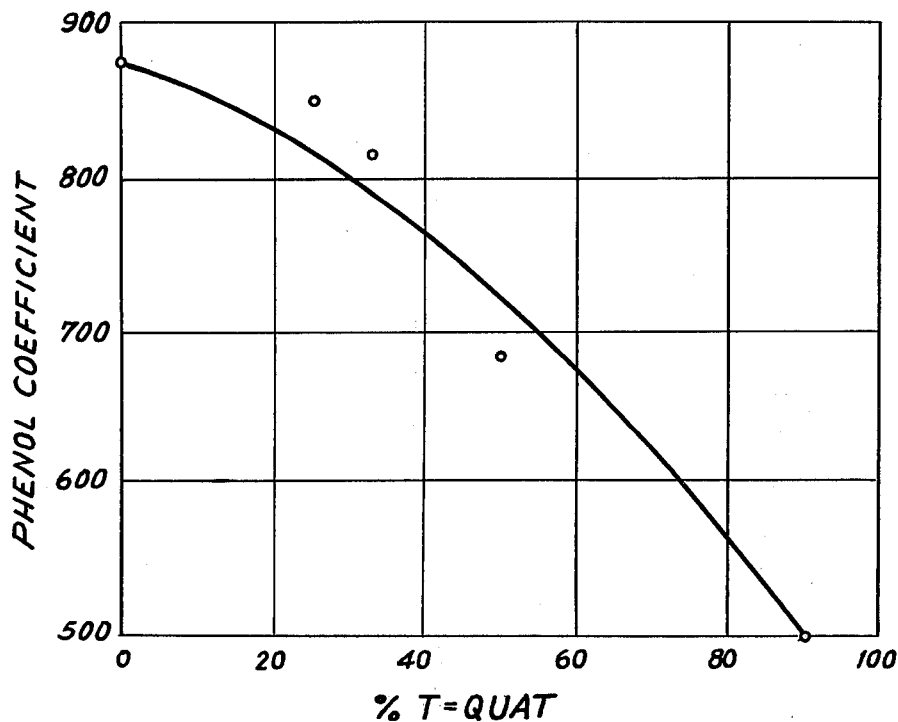
FIG. 1 is a graph relating the content of T-QUAT in a bactericidal composition to the phenol coefficient of said composition.

The compound tris(2-hydroxyethylamine) benzyl ammonium chloride, i.e., T-QUAT, is readily synthesized by essentially standard procedures. Thus, 1 mol of tris(2-hydroxyetyl) amine (triethanolamine) is mixed with 1 mol of benzyl chloride and warmed slightly with agitation. The reaction is exothermic, and the temperature of the reaction vessel should be maintained by means of external or internal cooling in the range of 80° – 90° C for 1 – 2 hours. The product is cooled to 30°-20° C, and cold water is added to bring the solid content to any desired level, 50% being convenient. The temperature is then raised to 65° – 85° C for 1-2 hours after which the product is cooled, yielding a solution. The product may be used in this form.

In a second method of synthesis, the equimolar reactants may be dissolved in a lower alcohol such as isopropanol, and the reaction carried out in the presence of the solvent. The reactants are maintained, preferably at reflux temperature, untl the reaction is essentially complete. The product may be used in this form or diluted or concentrated as desired. Generally the quantity of alochol added to the reaction mixture is from 5 to 10% of the weight of the reactants.

It is also possible to synthesize the T-QUAT and an effective quaternary amine, that is, one having a high phenol coefficient, simultaneously. To carry out the reaction in this way, the compound to be quaternized is substituted mol for mol for a portion of the triethanolamine. Again, the mixture need not be purified. Also, the mixture is conveniently used in solution in water and alcohol. A suitable composition is 80% of quaternary amines, 10% water and 10% alcohol, all by weight.

Among the most frequently used quaternary amines are the so-called benzalkonium chlorides, these being the adducts of benzyl chloride and alkyl dimethyl amine. Such a material is commercially designated as DMMCD, and is made by Armak Chemical Company, a division of Akzona, Inc. The amine is derived from the middle cut of a coconut oil distillate. The alkyl groups in DMMCD lie principally in the range of $C_{10}$ to $C_{16}$. Further, the groups are normal alkyl.

The level of bactericidal activity appears to be associated both with the length of the chain and whether the chain is normal or branched, the normal-alkyl groups, in general, being more commonly used. Also, the range of $C_{12}$ to $C_{16}$ is considered optimal for this type of quaternary amine.

As is well-known, the effectiveness of these quaternary amines is generally expressed in terms of the phenol coefficient, this term referring to the factor by which the compound can be diluted and still have an effectiveness equal to that of phenol. Quaternary amines based on DMMCD have a phenol coefficient of about 880. The average of 3 tests was 883.

As aforenoted, the phenol coefficient of T-QUAT is less than 1 so that it is essentially negligible. Surprisingly, blends of T-QUAT and quaternary amines, as exemplified by the benzalkonium chlorides in FIGS. 1 and 2, have phenol coefficients which are substantially above the weighted average of the components, said weighted average being the percentage of benzalkonium chloride times its phenol coefficient plus the percentage of T-QUAT times its phenol coefficient.

FIG. 1 shows the phenol coefficients of various blends of T-QUAT and benzalkonium chloride based on DMMCD. IT will suffice to call attention to the blend of 9 parts of T-QUAT and 1 part of the benzalkonium chloride, the product having a phenol coefficient of 500, whereas, based on the weighted average of the components, the blend should have a phenol coefficient of about 97. Consequently, instead of it being necessary to utilize 883/97 pounds of blend to replace 1 pound of the pure quaternary amine, it is necessary to use only 883/500 pounds. Since the cost of the high-coefficient quaternary amine is more than 3 times that of T-QUAT, it is evident that a substantial saving can be effected by the use of the blend.

Figure 2:
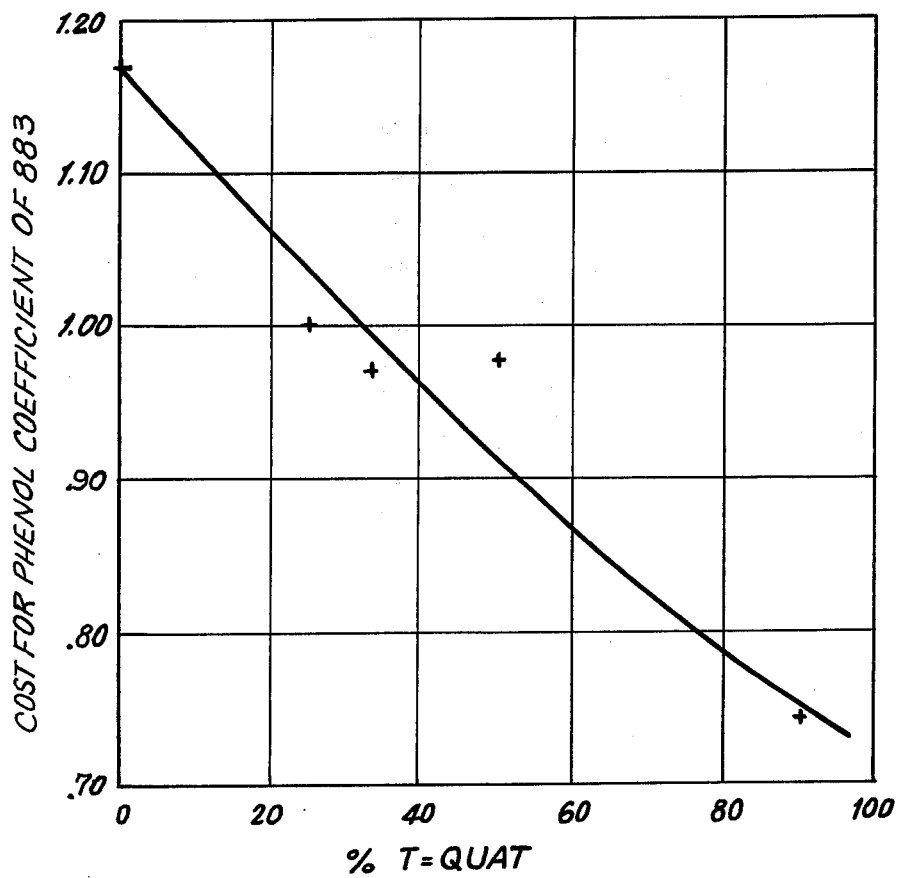
FIG. 2 is a graph relating the content of T-QUAT to the cost of achieving a phenol coefficient equivalent to that of a quaternary amine alone.

The base price of the quaternary amine prepared from DMMCD is 1.174 dollars per pound. That of T-QUAT is .337 dollars per pound. The cost of blend necessary to achieve a bactericidal activity equivalent to that of the high-coefficient quaternary when used alone is shown in FIG. 2. As can be seen, the 90% T-QUAT blend when used at a concentration to give a level of bactericidal activity comparable to that of the quaternary amine alone is only about 74 cents. The reduction in cost achieved through the use of the blend is therefore in excess of 36%.

When used in swimming pools, the blends of the T-QUAT and the quaternary amine based on DMMCD are used at a level of from one-half to two ppm. They can, of course, be used at substantially higher levels in order to achieve greater activity. Other quaternary amines which have been found to be useful in combination with T-QUAT include the alkyl trimethyl ammonium chlorides. Where the alkyl groups principally contain from 10 to 18 carbon atoms, the phenol coefficient is about 300. This composition is sold as Arquad 12-50 and is made by Armak Chemical Company, a division of Akzona, Inc. It is also derived from coconuts. Again, where the alkyl groups contain fewer than 10 carbon atoms and more than 18 carbon atoms, they are also somewhat effective as are the branched chain compounds as well. Another family of quaternary amines is that consisting of the adducts of the alkyl-substituted imidazoles.

The quaternary amines, includes T-QUAT come under the Federal Rodenticide Act. T-QUAT in conjunction with DMMCD has been registered with the Environmental Protection Agency. Tests for activity against Chlorella pyrenoidosa and Phormidium retzii and Phormidium inundadum were made by the standard Fitzgerald technique. Tests were also carried out by the Official A.O.A.C. test method on Staphylococcus aureus using a subculture medium Letheen broth at a temperature of 20° C.

T-QUAT, by itself is an effective algicide. Thus, Hyamine 3500 made by Rohm & Hass at 5 ppm and 2.5 ppm had 64.15 and 46.5% inhibition of Chlorella pyrenoidosa on a test which was an adaptation of the Fitzgerlad method. Corresponding values for T-QUAT at the same concentrations were 42.9 and 23.5%. Though not at effective as the Hyamine 3500, its tendency to foam is much lower, a factor of importance in recirculating industrial cooling systems.

As aforenoted, in the alkyl-substituted quaternary amines, greatest phenol coefficient is associated with the range of 12 to 16 carbon atoms. Yet, T-QUAT has no chain longer than 2 carbon atoms in it, and, moreover, includes 3 hydroxyl groups. Consequently, it would be expected then it would have a low phenol coefficient, as it does, in fact, It is all the more surprising, therefore, that there is such strong synergism between this quaternary amine and the quaternary amines of high phenol coefficient.

It will thus be seen that the objects set forth above, among those made apparent from the preceding description, are efficiently attained and, since certain changes may be made in compositon set forth without departing from the spirit and scope of the invention it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A composition useful as a bactericide and an algicide, comprising a mixture of tris (2-hydroxyethyl) benzyl ammonium chloride, and an n-alkyl dimethyl benzalkonium chloride, wherein said n-alkyl group is 10 to 18 carbon atoms in length, the ratio of said tris (2-hydroxyethyl)benzyl ammonium chloride to said benzalkonium chloride being such that the phenol coefficient of the mixture is substantially higher than the weighted average of the components.

2. The composition as defined in claim 1, wherein said n-alkyl group is 12 to 16 carbon atoms in length.

3. The composition as defined in claim 1, wherein said composition includes a solvent for said tris (2-hydroxyethyl) benzyl ammonium chloride and said benzalkonium chloride.

4. The product of the reaction at between about 80° and 90° C for 1 to 2 hours of triethanolamine and another tertiary amine with a quantity of benzyl chloride equivalent to said triethanolamine and tertiary amine, said other tertiary amine being such that the reaction product of same with said benzyl chloride is a benzalkonium chloride having a phenol coefficient substantially higher than 1, said other tertiary amine being an n-alkyl dimethyl compound, said n-alkyl group being 10 to 18 carbon atoms in length, the ratio of triethanolamine to said other tertiary amine being such that the phenol coefficient of the product is substantially higher than the weighted average of the components of said product.

5. The reaction product as claimed in claim 4 wherein said n-alkyl group is 12 to 16 carbon atoms in length.

* * * * *